United States Patent
Wittmann et al.

(10) Patent No.: US 10,175,166 B1
(45) Date of Patent: Jan. 8, 2019

(54) METHOD FOR OPERATING AN OPTICAL MEASURING SYSTEM FOR MEASURING THE CONCENTRATION OF A GAS COMPONENT IN A MEASURED GAS

(71) Applicant: Axetris AG, Kägiswil (CH)

(72) Inventors: Andreas Wittmann, Giswil (CH); Sven Schlesinger, Sachseln (CH); Torsten Platz, Weggis (CH)

(73) Assignee: Axetris AG, Kägiswil (CH)

( * ) Notice: Subject to any disclaimer, the term of this patent is extended or adjusted under 35 U.S.C. 154(b) by 0 days.

(21) Appl. No.: 15/928,425

(22) Filed: Mar. 22, 2018

(51) Int. Cl.
*G01N 21/39* (2006.01)

(52) U.S. Cl.
CPC ... *G01N 21/39* (2013.01); *G01N 2201/06113* (2013.01)

(58) Field of Classification Search
CPC .......................................................... G01N 21/39
USPC ........................................................... 356/437
See application file for complete search history.

(56) References Cited

U.S. PATENT DOCUMENTS

| | | | |
|---|---|---|---|
| 5,026,991 A * | 6/1991 | Goldstein | G01N 21/39 250/339.04 |
| 5,202,570 A * | 4/1993 | Tanaka | G01N 21/39 250/205 |
| 5,301,014 A | 4/1994 | Koch | |
| 6,618,148 B1 * | 9/2003 | Pilgrim | G01N 21/1702 250/339.09 |
| 2012/0281221 A1 * | 11/2012 | Studer | G01J 3/02 356/437 |
| 2014/0247843 A1 | 9/2014 | Steinbacher | |

FOREIGN PATENT DOCUMENTS

| | | |
|---|---|---|
| DE | 4110095 A1 | 10/1992 |
| DE | 102013202289 A1 | 8/2014 |
| EP | 2848918 A1 | 3/2015 |

OTHER PUBLICATIONS

European Search Report for corresponding European Application No. 18163424, dated Aug. 29, 2018.

\* cited by examiner

*Primary Examiner* — Roy M Punnoose
(74) *Attorney, Agent, or Firm* — Renner Otto Boisselle & Sklar, LLP

(57) ABSTRACT

A method for operating an optical measuring system for measuring the concentration of a gas component in a measured gas, based on wavelength modulation spectroscopy, wherein a laser light source is operated in a current-modulated manner with a base current $I_{DC}$ and a modulation current $I_{AC}$ and a laser beam of the wavelength $\lambda_0$ having a wavelength modulation amplitude $\Delta\lambda_{AC}$ is emitted, and the wavelength modulation amplitude $\Delta\lambda_{AC}$ of the laser light is kept constant by way of variable setting of the current modulation amplitude $\Delta I_{AC}$. The method provides for keeping a modulated power $\Delta P_{AC}$ at an internal resistor $R_I$ of the laser light source constant at the operating point so as to stabilize the wavelength modulation amplitude $\Delta\lambda_{AC}$.

7 Claims, 4 Drawing Sheets

METHOD FOR OPERATING AN OPTICAL MEASURING SYSTEM FOR MEASURING THE CONCENTRATION OF A GAS COMPONENT IN A MEASURED GAS

TECHNICAL FIELD

The invention relates to a method for operating an optical measuring system for measuring the concentration of a gas component in a measured gas, based on wavelength modulation spectroscopy, comprising a wavelength-tunable temperature-stabilized laser light source, which periodically varies a central base wavelength $\lambda_0$ of the laser light of the laser light source by changing the base current via a relevant absorption line of the gas component at an operating point and, at the same time, modulates the same with a frequency (f) and a determinable amplitude by way of a modulation device, a light detector, which detects the intensity of the laser light after having passed through the measured gas, and an evaluation device, which comprises means for the phase-sensitive demodulation of a measuring signal generated by the light detector at the frequency (f) and/or one of the harmonics thereof, wherein the laser light source is operated in a current-modulated manner with a base current $I_{DC}$ and a modulation current $I_{AC}$ and emits a laser beam of the wavelength $\lambda_0$ having a wavelength modulation amplitude $\Delta\lambda_{AC}$, and the wavelength modulation amplitude $\Delta\lambda_{AC}$ of the laser light is kept constant by way of variable setting of the current modulation amplitude $\Delta I_{AC}$.

BACKGROUND ART

Optical measuring systems for measuring the concentration of a gas component in a measured gas, based on wavelength modulation spectroscopy, are known from the prior art in a wide variety of embodiments, as are a multitude of different methods for operating such an optical measuring system.

In tunable laser absorption spectroscopy (TLAS), and in particular wavelength modulation spectroscopy (WMS), the wavelength modulation amplitude generally plays an important role. This is defined by way of setting of the current modulation amplitude during calibration for the operating point. However, changes to the operating point or long-term changes in the laser cause the wavelength modulation amplitude to change (despite the current modulation amplitude remaining the same). As a consequence, the change in the wavelength modulation amplitude also causes the sensor calibration to deviate from the specification limits, which then often necessitates re-calibration of the optical measuring system.

In the optical measuring systems of the type in question, in the case of changes to the operating mode or long-term changes in the laser light source compared to the time of calibration, for the purpose of stabilization of the sensor accuracy, it is known to re-set the wavelength modulation amplitude during operation by adapting the intensity of the modulation current for the laser light source, which is to say the current modulation amplitude, so that the wavelength modulation amplitude once again at least approximately corresponds to the time of calibration. Reference is made in this regard to document EP 2 610 608 B1, by way of example.

Document EP 2 610 608 B1 discloses a gas measuring device for measuring a target gas and a method for setting the width of a wavelength modulation of the gas measuring device, comprising a light source and a detection unit, by oscillating a a laser light wavelength by way of the source, so as to have a central wavelength determined by a main current, and so as to be modulated according to a modulation current at an oscillation frequency, and with a wavelength modulation width, with the central wavelength being varied by changing the main current in a longer cycle than that of the modulation current, whereby the detection unit outputs a signal according to an intensity of the laser light transmitted through a standard gas. The method furthermore comprises a step of obtaining a detection signal by detecting the laser light transmitted through the standard sample, with the central wavelength being varied, the step of obtaining a specific frequency component of the detection signal that is oscillated at a frequency that is a positive integral multiple of an oscillation frequency of the modulation current, and a step of calculating a ratio of a magnitude of a local minimum of the specific frequency component with respect to the central wavelength of the laser light and a magnitude of a local maximum of the specific frequency component with respect to the central wavelength of the laser light, and a step of setting the width of the wavelength modulation of the laser light so that the ratio satisfies a predetermined condition. This is a condition where the ratio that corresponds to the width of the wavelength modulation equals a predetermined target value on one-to-one basis. During the setting of the modulation width of the laser light, the width of the wavelength modulation is set by adapting an intensity of the modulation current.

SUMMARY

Proceeding from this, it is the object of the claimed invention to propose a different, simpler, and more precision option for keeping the wavelength modulation amplitude constant, despite changing laser properties, such as temperature, operating current or long-term drift.

This object is achieved according to the invention by a method for operating an optical measuring system for measuring the concentration of a gas component in a measured gas, based on wavelength modulation spectroscopy, having the features described herein.

In optical measuring systems for measuring the concentration of a gas component in a measured gas, based on wavelength modulation spectroscopy, the wavelength modulation amplitude $\Delta\lambda_{AC}$ is the crucial parameter that is set during the calibration of the sensor by way of the current modulation amplitude $\Delta I_{AC}$ for the selected operating point $I_{DC}$. Deviations from the operating point, for example as a result of a change in the outside temperature relative to the calibration temperature or as a result of wavelength drift due to aging of the laser, however, cause the wavelength modulation amplitude to change. The sensor accuracy consequently decreases, necessitating re-calibration in some circumstances.

The core idea of the invention is, during operation of the measuring system at the intended operating point, to stabilize the wavelength modulation amplitude $\Delta\lambda_{AC}$ of the laser light, using operating parameters that were set for the operating point at the time of calibration of the laser light source, preferably a laser diode, and then recorded and stored, and voltages and/or currents at the laser light source measured during operation. In the development of the novel method it was found that the wavelength modulation amplitude $\Delta\lambda_{AC}$ is proportional to the modulated AC power $\Delta P_{AC}$.

$$\Delta P_{AC} \sim \Delta\lambda_{AC} \qquad \text{(formula 1)}$$

According to the invention, the wavelength modulation amplitude $\Delta\lambda_{AC}$ of the laser light is thus kept constant by way of variable setting of the current modulation amplitude $\Delta I_{AC}$ by keeping a modulated power $\Delta P_{AC}$ of the laser light at an internal resistor $R_I$ of the laser light source constant at the operating point. For this purpose, the voltage at the laser light source is measured, among other things.

It is commonly known that each laser light source circuit diagram can be replaced with an equivalent circuit, which comprises a laser emitter (active zone) and an internal resistor $R_I$ connected in series thereto. As soon as a base current $I_{DC}$ modulated with a modulation current $I_{AC}$ flows through the laser light source, a voltage $U_L$ is present at the laser light source, which in part drops across the laser emitter as a partial voltage $U_E$ and across the internal resistor $R_I$ as a partial voltage $U_{Ri}$.

For the calculation of the modulated power, the voltage across the laser $U_L$ is not relevant, only the voltage $U_{Ri}$ that has dropped across the internal resistor $R_I$ is relevant. The power modulation amplitude $\Delta P_{AC}$ is calculated as follows:

$$\Delta P_{AC} = \Delta I_{AC} \cdot U_{Ri} = \Delta I_{AC} \cdot R_I \cdot I_{DC} \quad \text{(formula 2)}$$

where $\Delta I_{AC}$ denotes the current modulation amplitude, and $U_{Ri}$ represents the voltage that has dropped across the internal resistor. Alternatively, the voltage can also be calculated via the value of the internal resistor $R_I$ and the DC laser current $I_{DC}$ flowing through the same.

The DC voltage across the internal resistor $R_I$ is given by $$U_{Ri} = U_L - U_E \quad \text{(formula 3)}$$

where $U_E$ has a value of 0.9 to 1.1 V, depending on the laser type (having a wavelength close to that common in the telecom industry).

In general, it must be noted that, during operation of the optical measuring system in an environment that is not thermally stabilized, a change in the ambient temperature causes the laser light source of the sensor to assume a slightly higher or lower temperature. The target wavelength of the sensor thus shifts toward a lower or higher DC laser current $I_{DC}$. As a result, the power modulation amplitude $\Delta P_{AC}$ according to formula 2 also changes. The consequence of this change in the power modulation amplitude is that, according to formula 1, the wavelength modulation amplitude therefore also changes $\Delta\lambda_{AC}$.

Even if the DC laser current $I_{Dc}$ is constant, the power modulation amplitude $\Delta P_{AC}$ may change if the internal resistance $R_I$ of the laser light source changes during operation due to various (long-term) influencing factors.

So as to ensure that the laser light source is operated at the same wavelength modulation amplitude $\Delta\lambda_{AC}$ at any given time, according to the invention the instantaneous power modulation amplitude $\Delta P_{AC\_Act}$ is kept equal to the power modulation amplitude $\Delta P_{AC\_Calib}$ at the time of calibration of the optical measuring system.

$$\Delta P_{AC\_Act} = \Delta P_{AC\_Calib} \quad \text{(formula 4)}$$

Using formula 2 in formula 4 and then solving the equation for the instantaneous current modulation amplitude $\Delta I_{AC\_Act}$ results in $$\Delta I_{AC\_Act} = \Delta I_{AC\_Calib} \cdot U_{Ri\_Calib} / U_{Ri\_Act} \quad \text{(formula 5)}$$

wherein the ratio of the calibrated values to the instantaneous voltage values is found. Formula 5 can be solved even further. The voltage $U_{Ri}$ at the internal resistor $R_I$ can be represented as $U_L - U_E$ according to formula 3.

In a preferred embodiment of the method according to the invention, the current modulation amplitude $\Delta I_{AC}$ is accordingly adapted, taking a current modulation amplitude $\Delta I_{AC\_Calib}$ that was set during the calibration of the laser light source into consideration, such that the modulated power modulation amplitude $\Delta P_{AC}$ is kept constant.

For stabilizing the wavelength modulation amplitude $\Delta\lambda_{AC}$, in an advantageous embodiment of the invention, the voltage change $\Delta U_{Ri}$ at the internal resistor $R_I$ of the laser light source is preferably determined by adapting the current modulation amplitude $\Delta I_{AC}$, wherein the adaptation of the current modulation amplitude $\Delta I_{AC}$ is based on the quotient of $U_{L\_Calib}$ and $U_{L\_Act}$.

In a particularly favorable variant of the method according to the invention, the internal resistance $R_I$ of the laser light source is advantageously determined from a voltage/current characteristic curve of the laser light source in which the voltage drop $U_L$ across the laser light source is recorded as a function of the base current $I_{DC}$. The voltage/current characteristic curve of the laser light source is usually recorded for the first time during the calibration of the optical measuring system. This may be repeated later if needed, for example during a renewed calibration or for monitoring during normal operation.

In one embodiment of the invention, at least the modulated power $\Delta P_{AC}$ of the laser light source is ascertained during the calibration of the optical measuring system. Instead of the power $\Delta P_{AC}$, it is also possible to use the amplitude $\Delta I_{AC}$ of the modulation current $I_{AC}$ and the voltage drop $U_I$ across the internal resistor $R_I$. As an alternative, it is also possible to ascertain the amplitude $\Delta I_{AC}$ of the modulation current $I_{AC}$, the internal resistance $R_I$ and the base current $I_{DC}$ at the operating point. The respective ascertained parameters are stored at the time of calibration. The base current $I_{DC}$ determines the operating point of the optical measuring system. During ongoing operation, this allows deviations in this regard to be easily detected, and also allows for response according to the above-described method.

The optical measuring system used to carry out the method according to the invention for measuring the concentration of a gas component in a measured gas, based on wavelength modulation spectroscopy, comprises a wavelength-tunable temperature-stabilized laser light source, and preferably a semiconductor laser light source in the form of a laser diode, which periodically varies a central base wavelength $\lambda_0$ of the laser light of the laser light source via a relevant absorption line of the gas component at an operating point, for example in a ramp-like manner (sawtooth) and, at the same time, modulates the same with a frequency (f) and an amplitude by way of a modulation device. The measuring system moreover comprises a light detector, which detects the intensity of the laser light after having passed through the measured gas, and an evaluation device, which comprises means for the phase-sensitive demodulation of a measuring signal generated by the light detector at the frequency (f) and/or one of the harmonics thereof. The modulation may be sinusoidal or triangular, for example. The laser light source is operated in a current-modulated manner with a base current $I_{DC}$ and a modulation current $I_{AC}$ and emits a laser beam of the wavelength $\lambda_0$ having a wavelength modulation amplitude $\Delta\lambda_{AC}$. The wavelength modulation amplitude $\Delta\lambda_{AC}$ of the laser light is kept constant by way of variable setting of the current modulation amplitude $\Delta I_{AC}$ by the evaluation device, in conjunction with the modulation device.

During the calibration and during regular operation of the optical measuring system for determining the concentration of a gas component, an evaluation device comprising lock-in technology is preferably used so as to achieve noise reduction in the known manner, in particular in order to considerably lower the noise caused by the 1/f signal. The design and operating principles of a lock-in amplifier are generally known to a person skilled in the art, making it unnecessary to provide fvull description thereof. Summarized briefly, a lock-in amplifier, which sometimes is also referred to as a phase-sensitive rectifier or carrier frequency amplifier, is an amplifier for measuring a weak electrical alternating signal, which is modulated with a reference signal having a known frequency and phase. The device represents an extremely narrow-band bandpass filter, thereby improving the signal-to-noise ratio. The advantage when using such a device is that DC voltages and AC voltages having different frequencies and noise are efficiently filtered.

The method according to the invention requires an electrical line from the laser light source to the evaluation unit so as to ascertain the power modulation amplitude $\Delta P_{AC}$ of the laser light via the internal resistance $R_I$ of the laser light source as exactly as possible. If this line is not present in an optical measurement system intended for use of the proposed novel method, a hardware adaptation is necessary, or else this method cannot be employed. The composition of an optical measuring system that is suitable for determining the voltage at the internal resistor of the laser light source via a voltage measurement at the laser light source, and to subsequently adapt the current modulation amplitude $\Delta I_{AC\_Act}$ therefrom so as to stabilize the wavelength modulation amplitude $\Delta \lambda_{AC}$ of the laser light, will be briefly described again hereafter based on a schematic illustration.

The calibration of the optical measuring system takes place substantially according to the common method that is routine to the person skilled in the art, by way of a known reference gas, which is to be detected as the measured gas by the optical measuring system during regular operation, and the concentration of which is to be measured. So as to establish the operating point, first the laser light source is operated using a common base current $I_{AC}$ and modulation current $I_{AC}$, and the temperature of the temperature-stabilized laser light source is varied until an absorption signal for the reference gas is detected. Thereafter, the base current $I_{DC}$ is current-modulated with a modulation current $I_{AC}$ at the ascertained temperature, which is temperature-stabilized by way of a Peltier element, for example, so that the laser light source emits a laser beam of the wavelength $\lambda_0$ having a wavelength modulation amplitude $\Delta \lambda_{AC}$. Thereafter, the current modulation amplitude or the wavelength modulation amplitude can be optimized according to various criteria of the measuring system, for example an optimal signal-to-noise ratio. This is necessary, in particular, since the wavelength modulation amplitude $\Delta \lambda_{AC}$ changes with the base current $I_{DC}$. As the base current rises, the wavelength modulation amplitude of the laser light increases, which is to say, below a selected operating point this is smaller than above the operating point, and therefore must be established separately for each operating point.

This fundamental procedure also includes the consideration of measures during the wavelength modulation spectroscopy which are suitable for entirely or partially suppressing optical interference phenomena. In this way, the wavelength modulation amplitude or the current modulation amplitude is fundamentally established, based on various criteria of the measuring system and of the gas to be detected. The accordingly modulated power, which is to say the power modulation amplitude $\Delta P_{AC}$, or an equivalent variable, such as the modulation current and the voltage of the laser light source, is also ascertained at the time of calibration, and is stored.

The features and feature combinations mentioned above in the description, and the features and feature combinations mentioned hereafter in the description of the figures and/or shown only in the figures, can be used not only in the respective indicated combinations, but also in other combinations, or alone. It is not necessary for all the features recited in the claims to be implemented to carry out the invention. It is also possible to replace individual features of the independent or dependent claims with other disclosed features or feature combinations.

BRIEF DESCRIPTION OF THE DRAWINGS

The invention will be described again in more detail hereafter based on the accompanying drawings: In the drawings in schematic illustrations.

DETAILED DESCRIPTION OF the Invention

Figure 1:
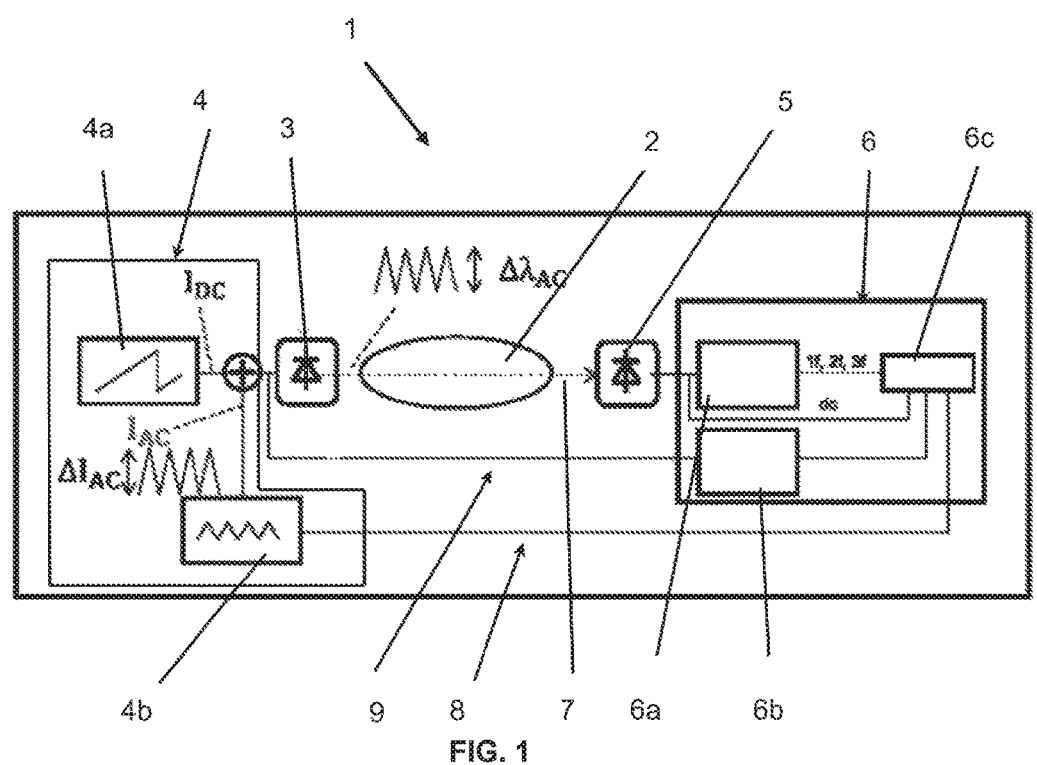
FIG. 1 shows an optical measuring system suitable for carrying out the method according to the invention.

FIG. 1 schematically shows the basic design of an optical measuring system 1 for measuring the concentration of a gas component in a measured gas 2, based on wavelength modulation spectroscopy. The measuring system 1 comprises a wavelength-tunable temperature-stabilized laser light source 3, a modulation device 4, a light detector 5, and an evaluation device 6. The laser light source 3 emits a laser beam 7 of the wavelength $\lambda_0$ having a wavelength modulation amplitude $\Delta \lambda$Ac. The modulation device 4 periodically varies the central base wavelength $\lambda_0$ of the laser light of the laser light source 3 via a relevant absorption line of the gas component at an operating point and, at the same time, modulates the same in a triangular manner with a frequency (f) and an amplitude. This additionally comprises at least one DC and/or AC voltage source or a DC and AC current source 4a, and associated modulation means 4b for operating the laser light source 3. The modulation device 4 is connected directly to the laser light source 3. The light detector 5 detects the laser beam 7 originating from the laser light source 3 after this has passed through the measured gas 2, and generates a reception signal, which is dependent on the intensity of the laser light after it has passed through the measured gas 2, and is supplied to the evaluation unit 6. The evaluation unit 6 comprises means for the phase-sensitive demodulation of a measuring signal generated by the light detector 5 at the frequency (f) and/or one of the harmonics thereof. The evaluation unit 6 comprises two lock-in amplifiers 6a, 6b and a processing unit 6c. The processing unit 6c evaluates the demodulated reception signal of the light detector 5 and, as a function thereof, controls the modulation means 4b of the modulation device 4 so as to keep the wavelength modulation amplitude $\Delta \lambda_{AC}$ of the laser light constant by adapting the current modulation amplitude $\Delta I_{AC}$. For this purpose, this comprises an electrical control line 8 to the modulation device 4. Furthermore, an electrical connecting line 9 leads from the laser light source 3 to the lock-in amplifier 6b, by way of which the voltage present at the laser light source 3 is detected and evaluated. In the evaluation, the above-described formulas 1 to 5 are used, among other things.

Figure 2:
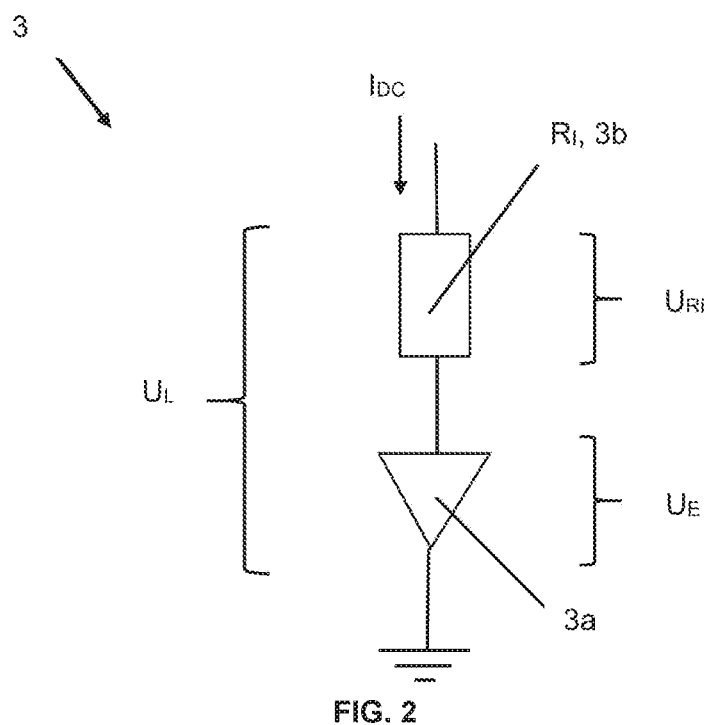
FIG. 2 shows the equivalent circuit for the laser light source.

FIG. 2 shows the equivalent circuit for the laser light source 3. The laser light source 3 can thus be replaced for calculation purposes with a light emitter 3a, and an internal resistor $R_I$, 3b connected in series thereto. The laser light source 3 is operated in a current-modulated manner with a base current $I_{DC}$ and a modulation current $I_{AC}$. Voltage $U_L$ is present at the laser light source 3 and drops partially across the internal resistor 3b as a partial voltage $U_{Ri}$, and across the light emitter 3a as a partial voltage $U_E$.

Figure 3:
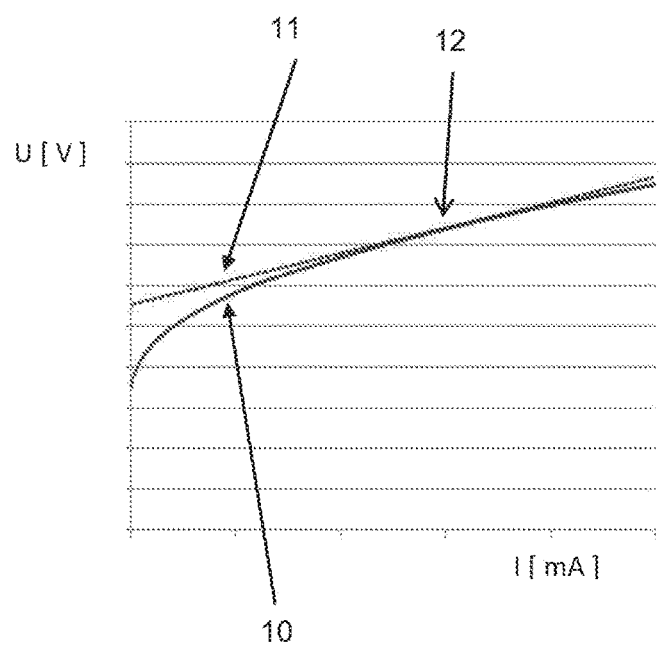
FIG. 3 shows a recorded voltage/current characteristic curve for determining the internal resistance of the laser light source.

FIG. 3 illustrates a current/voltage characteristic curve 10 recorded during the calibration of the optical measuring system 1 for determining the internal resistance $R_I$ of the laser light source 3. The internal resistance $R_I$ is determined from the relationship of the current/voltage characteristics of the laser light source 3 at the operating point 12. For this purpose, the current/voltage characteristic curve 10 (solid line) is provided with a linear approximation line 11 (dotted line) at the operating point 12 for determining the internal resistance $R_I$. The slope of the approximation line 11 corresponds to the internal resistance $R_I$, 3b at the operating point 12.

Figure 4:
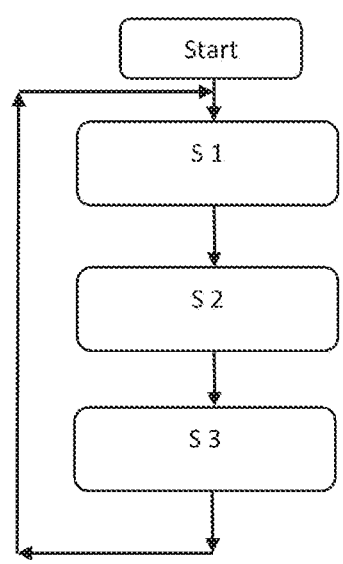
FIG. 4 shows a flow chart for adapting the current modulation amplitude.

FIG. 4 illustrates a flow chart for adapting the current modulation values, wherein the determination of the instantaneously modulated power is either carried out on the DC laser current which is assigned to the maximum of the absorption signal, or is ascertained via multiple DC laser current values of the scan of the measurement. In general, multiple scans are carried out via the relevant absorption line, which is to say the corresponding central base wavelength $\lambda_0$ of the laser light of the laser light source is periodically varied multiple times via the absorption line of the gas component at the operating point 12, and at the same time is modulated, wherein a number of measuring points are usually recorded and arithmetically evaluated. The current modulation amplitude may be kept for each measuring point or may be calculated from the calculation of the instantaneous measuring point so as to optimize the result for the next measuring point. In the procedure shown symbolically in FIG. 4, which reflects the present operation of the optical measuring system, the instantaneous modulated AC power at the internal resistor $R_I$ is established in a first method step S1. In the subsequent second method step S2, thereafter, the instantaneous current modulation value is determined. In the next subsequent third method step S3, thereafter, the actual concentration measurement for the measured gas takes place using the instantaneous current modulation value. The method steps S1 to S3 are carried multiple times in a loop, wherein, if necessary, the current modulation amplitude $\Delta I_{AC}$ may be adapted between the runs if the instantaneous current modulation value $\Delta I_{AC\_Act}$ deviates from the ideal current modulation value $\Delta I_{AC\_Calib}$ during the calibration of the optical measuring system, and thus the wavelength modulation amplitude $\Delta \lambda_{AC}$ is changed compared to the calibration.

The invention claimed is:

1. A method for operating an optical measuring system for measuring the concentration of a gas component in a measured gas, based on wavelength modulation spectroscopy, comprising a wavelength-tunable temperature-stabilized laser light source, which periodically varies a central base wavelength $\lambda_0$ of the laser light of the laser light source via a relevant absorption line of the gas component at an operating point and, at the same time, modulates the same with a frequency (f) and an amplitude, by way of a modulation device, a light detector, which detects the intensity of the laser light after it has passed through the measured gas, and an evaluation device, which comprises means for the phase-sensitive demodulation of a measuring signal generated by the light detector at the frequency (f) and/or one of the harmonics thereof, the laser light source being operated in a current-modulated manner with a base current $I_{DC}$ and a modulation current $I_{AC}$ and emitting a laser beam of the wavelength $\lambda_0$ having a wavelength modulation amplitude $\Delta \lambda_{AC}$, and the wavelength modulation amplitude $\Delta \lambda_{AC}$ of the laser light being kept constant by way of variable setting of the current modulation amplitude $\Delta I_{AC}$, wherein the voltage at the laser light source is measured at the operating point, and based thereon a modulated power $\Delta P_{AC}$ at an internal resistor $R_I$ of the laser light source is kept constant.

2. The method according to claim 1, wherein the current modulation amplitude $\Delta I_{AC}$ is adapted, taking a current modulation amplitude $\Delta I_{AC\_Calib}$ that was set during the calibration of the laser light source into consideration, such that the modulated power modulation amplitude $\Delta P_{AC}$ is kept constant.

3. The method according to claim 1, wherein the voltage change $\Delta U_{Ri}$ at the internal resistor $R_I$ of the laser light source is determined by adapting the current modulation amplitude $\Delta I_{AC}$ so as to stabilize the wavelength modulation amplitude $\Delta \lambda_{AC}$.

4. The method according to claim 3, wherein the adaptation of the current modulation amplitude $\Delta I_{AC}$ is based on the quotient of $U_{L\_Calib}$ and $U_{L\_Act}$.

5. The method according to claim 1, wherein, during the calibration of the optical measuring system, the modulated power $\Delta P_{AC}$ of the laser light source, the amplitude $\Delta I_{AC}$ of the modulation current $I_{AC}$ and the voltage drop $U_I$ across the internal resistor $R_I$ or the amplitude $\Delta I_{AC}$ of the modulation current $I_{AC}$, the internal resistance $R_I$ and the base current $I_{DC}$ are ascertained at the operating point, and stored.

6. The method according to claim 1, wherein the internal resistance $R_I$ of the laser light source is determined from a voltage/current characteristic curve of the laser light source in which the voltage drop $U_L$ across the laser light source is recorded as a function of the base current $I_{DC}$.

7. The method according to claim 1, wherein an evaluation device comprising lock-in technology is used.

* * * * *